United States Patent [19]

Geisinger

[11] 4,045,070
[45] Aug. 30, 1977

[54] CONTAINER HANDLE

[76] Inventor: Wolfgang Geisinger, 180, rue Paradis, Rosemere, Quebec, Canada

[21] Appl. No.: 633,789

[22] Filed: Nov. 20, 1975

[30] Foreign Application Priority Data

Jan. 20, 1975 Canada .............................. 218239/75

[51] Int. Cl.² ............................................ B65D 23/10
[52] U.S. Cl. ............................... 294/31.2; 215/100 A
[58] Field of Search ....................... 215/100 R, 100 A;
294/31.2; 248/318; 150/48

[56] References Cited

U.S. PATENT DOCUMENTS

| | | | |
|---|---|---|---|
| 3,207,298 | 9/1965 | Wilson ................................ | 150/48 X |
| 3,220,591 | 11/1965 | Hidding ............................ | 215/100 A |
| 3,220,626 | 11/1965 | Tupper ............................. | 294/31.2 X |
| 3,307,752 | 3/1967 | Anderson ................. | 215/100 A UX |
| 3,311,252 | 3/1967 | Swartwood ...................... | 215/100 A |
| 3,463,536 | 8/1969 | Updegraff ................... | 215/100 A X |
| 3,653,610 | 4/1972 | Owen ........................... | 215/100 A X |
| 3,717,277 | 2/1973 | Stengle ............................. | 215/100 A |
| 3,744,658 | 7/1973 | Fujio ................................. | 215/100 A |

Primary Examiner—Donald F. Norton

[57] ABSTRACT

A handle made of thermoplastic material and consisting of an endless band and of a bail unitarily connected to the band. The bail includes a pair of arm portions having at each end thereof a flat connecting portion joined to generally diametrically opposed portions of the band and having a reduced cross-section compared to the cross-section of the remaining portion of the arm portion. The handle is used principally to suspend bottles for administering intravenous solution to patients and the particular construction of the handle insures that, when the bottle is in an inverted suspended position, it is in an accurate vertical position. This control for the vertical positioning of the bottle is obtained by a hinge action at the reduced cross-section portion of each arm.

5 Claims, 5 Drawing Figures

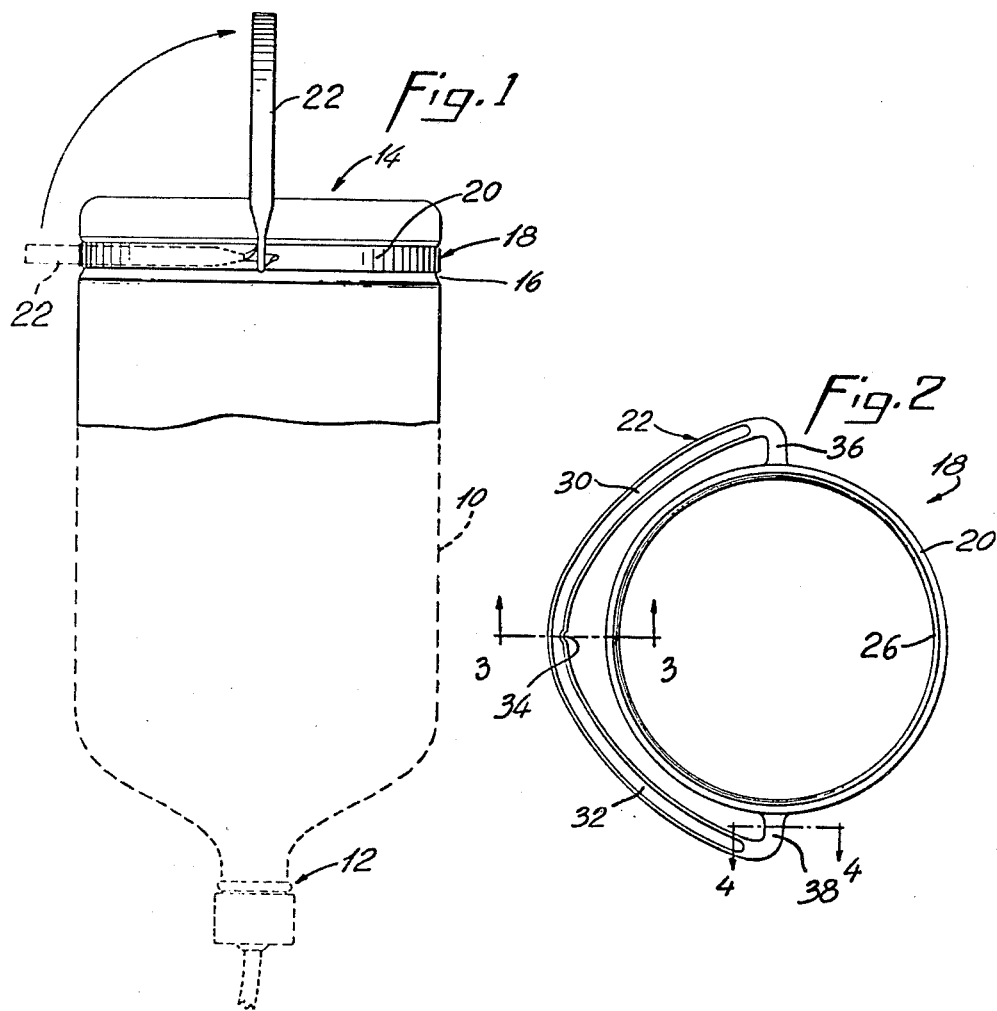
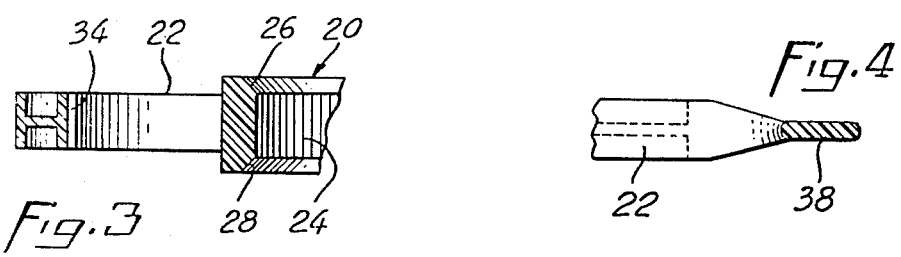
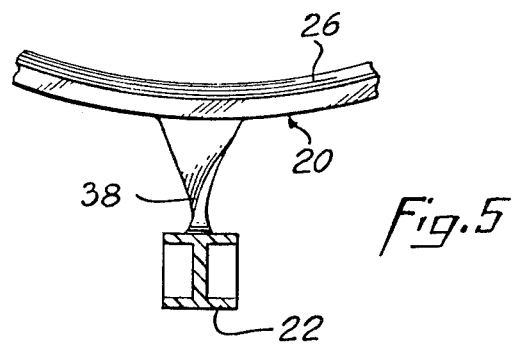

CONTAINER HANDLE

FIELD OF THE INVENTION

The present invention relates generally to handles; more particularly, the invention pertains to a handle for insuring the vertical positioning of inverted suspended bottles.

The control of the vertical positioning of pharmaceutical bottles, for example, used in the administering of intravenous solutions to patients is a continuing problem. At present, the only device, known to the inventor, which will provide an effective and true vertical positioning of these bottles is a metallic two-piece assembly, consisting of a bail and a collar by which the bail is attached to the bottle.

To greatly reduce costs and to avoid rust problems, one piece molded plastic handles have been made to overcome the problems associated with metal assemblies. One piece molded plastic handles, however, are formed (molded or stamped) with the bail and band disposed in the same plane. Hence, when a bottle, provided with a band made of elastomeric material, is suspended vertically, the characteristics of the plastic material provide an inherent tendency to return the bail in the same plane as the band. Therefore, as the solution inside the bottle is gradually administered, there is less gravity force opposing this tendency in the plastic material. As a result, when the solution level inside the bottle is low, the bottle is slightly tilted from its vertical dispensing plane thereby risking the introduction air in the intravenous solution being administered to the patient.

SUMMARY OF THE INVENTION

It is an object of this invention to provide a handle made of elastomeric material which will insure an effective control for the vertical positioning of a liquid dispensing bottle.

It is another object of this invention to provide a handle which is strong but resiliently stretchable for passage over one end of the bottle in order to be received firmly in a groove provided at the said end of the bottle.

It is still a further object of the present invention to provide a handle made of elastomeric material, the bail of which may rotate 90° relative to the plane of the band without creating in the material forces tending to alter the vertical positioning of a suspended bottle.

The present invention, therefore, relates to a handle for insuring the vertical positioning of an inverted suspended bottle having an external circumferential groove adjacent the bottom end thereof, the bottle being used principally for administering intravenous solutions to patients, comprising: an endless band of thermoplastic material which is resiliently stretchable for passage over the said bottom end of the bottle in order to be received in the groove firmly; a bail molded integrally with the band to form a unitary structure and including a pair of arm portions having at each end thereof a flat connecting portion joined to generally diametrically opposed portions of the band, each flat connecting portion extending in a plane parallel to the plane of the band and having a reduced cross-section compared to the cross-section of the remaining portion of the arm portion; the reduced cross-section providing a hinge between the bail and the band and allowing the bail to rotate 90° relative to the plane of the band to insure the vertical positioning of the bottle when suspended.

Other objects and further scope of applicability of the present invention will become apparent from the detailed description given hereinafter; it should be understood, however, that the detailed description, while indicating a preferred embodiment of the invention, is given by way of illustration only, since various changes and modifications within the spirit and scope of the invention will become apparent to those skilled in the art from this detailed description.

BRIEF DESCRIPTION OF THE DRAWINGS

FIG. 1 is an elevational view of a pharmaceutical bottle of the type used to contain intravenous solutions and on which a handle constructed in accordance with the present invention is shown in two positions;

FIG. 2 is a top plane view of the handle;

FIG. 3 is a cross-sectional view taken along lines 3—3 of FIG. 2;

FIG. 4 is a cross-sectional view taken along lines 4—4 of FIG. 2; and

FIG. 5 is an enlarged top cross-sectional view of the connecting portion between the bail and band.

DESCRIPTION OF THE PREFERRED EMBODIMENT

Referring now to the drawings, one embodiment of the invention will be described as applied to the bottom portion of an intravenous solution bottle 10. The bottle 10 includes a generally cylindrically body portion which terminates at one end in a neck opening 12 and which terminates at the other end in a closed bottom portion 14. Adjacent end portion 14, a circumferential groove 16 is formed on the exterior of the bottle; this groove is adapted to receive a handle, generally noted 18.

The handle 18 is formed of a thermoplastic material that is resilient, flexible and elastic; the handle consists of two portions: an endless band 20 and a bail 22. The band and the bail are formed together as a unitary assembly by means of a plastics forming operation, such as injection molding. Although polyethylene is a preferred example of a suitable thermoplastic material which is resistant to tearing, other functionally similar materials could be used satisfactorily for the handle 18.

The material of the handle must be resiliently stretchable for allowing the passage of the band 20 over the end 14 of the bottle in order to be received in the groove 16 firmly. Referring to FIG. 3, the inside wall 24 of the band may include at least one tapered edge, such as upper and lower edges 26 and 28, to allow easy insertion of the band in the groove. Also, once band 20 is received in groove 16, these edges correspondingly contact the sloping surfaces of the groove.

Bail 22 includes two arm portions 30 and 32. As shown in FIG. 3, these arm portions may have a H-shaped cross-section. At an intermediate point of the arm portions, a notch 34 may be provided on the inner wall of the bail to provide a seating arrangement for a support from which the bottle is to be suspended while at the same time insuring a relatively unshiftable bearing.

The arm portions 30 and 32 of the bail are connected to generally diametrically opposed portions of the band by means of flat connecting portions 36, 38, respectively.

Referring to FIG. 4, sections 36 and 38 are flat and extend in a plane parallel to the plane of the endless band 20. The cross-section of these sections 36 and 38 are reduced compared to the cross-section of the arm portions 30 and 32, as well as to the cross-section of the endless band 20. This reduced portion (see FIG. 5) allows a hinge action when the bail is rotated relative to the band. With this reduced cross-section in the flat connecting portion, the inherent resiliency in the plastic material tending to return the bail in its original position, i.e., in the same plane as the band, is considerably reduced and no longer affect the vertical positioning of the suspended bottle even if the level of intravenous solution in the bottle is low. Satisfactory results have been obtained where the ratio of thickness between the overall cross-section of the arm portions and that of the connection portion is 3:1.

What is claimed is:

1. A handle for insuring the vertical positioning of an inverted suspended bottle having an external circumferential groove adjacent one end thereof, said bottle being used principally for administering intravenous solutions to patients, comprising: an endless band of thermoplastic material, said material being resiliently stretchable for passage over said one end of said bottle to be received in said groove firmly; a bail molded integrally with said band to form a unitary structure, said bail including a pair of arm portions and; flat connecting portions joined respectively at the end of each arm portion to generally diametrically opposed portions of said band; each said flat connecting portion extending outward from said band in a plane parallel to the plane of said band and having a reduced cross-section and resiliency compared to the cross-section and resiliency of the arm portion, said reduced cross-section providing a twistable hinge at the junction between said bail and said band allowing said bail to rotate 90° relative to said plane of said band to insure the vertical positioning of said bottle when suspended.

2. A handle as defined in claim 1, wherein said bail has a notch at an intermediate point thereof to assist the positioning of said bottle on a support from which it is to be suspended.

3. A handle as defined in claim 1, wherein said cross-section of said connecting portion is reduced when compared to cross-section of said band.

4. A handle as defined in claim 1, wherein the inner wall of said endless band includes at least one tapered edge to assist the positioning of said band in said groove of said bottle.

5. A handle as defined in claim 1 wherein said arm portions have an H shape cross-section.

* * * * *